US008252949B2

(12) United States Patent
Seki et al.

(10) Patent No.: US 8,252,949 B2
(45) Date of Patent: Aug. 28, 2012

(54) PROCESS FOR PRODUCING FATTY ACID ESTERS

(75) Inventors: Yuichiro Seki, Wakayama (JP); Takanobu Katayama, Wakayama (JP); Katsutoshi Yamamoto, Wakayama (JP)

(73) Assignee: Kao Corporation, Tokyo (JP)

( * ) Notice: Subject to any disclaimer, the term of this patent is extended or adjusted under 35 U.S.C. 154(b) by 280 days.

(21) Appl. No.: 12/602,511

(22) PCT Filed: Jun. 11, 2008

(86) PCT No.: PCT/JP2008/061067

§ 371 (c)(1),
(2), (4) Date: Dec. 1, 2009

(87) PCT Pub. No.: WO2008/153186

PCT Pub. Date: Dec. 18, 2008

(65) Prior Publication Data

US 2010/0179338 A1 Jul. 15, 2010

(30) Foreign Application Priority Data

Jun. 11, 2007 (JP) ................................ 2007-154056

(51) Int. Cl.
*C07C 51/00* (2006.01)
*C07C 27/04* (2006.01)

(52) U.S. Cl. ........ 554/169; 554/170; 554/132; 554/176; 568/884; 568/885

(58) Field of Classification Search ........................ None
See application file for complete search history.

(56) References Cited

U.S. PATENT DOCUMENTS

| | | | | |
|---|---|---|---|---|
| 4,303,590 | A | 12/1981 | Tanaka et al. | |
| 5,120,700 | A | 6/1992 | Matsuda et al. | |
| 5,324,871 | A | 6/1994 | Carduck et al. | |
| 6,407,269 | B2 * | 6/2002 | Kaita et al. | 554/167 |
| 2003/0083514 | A1 | 5/2003 | Boocock | |
| 2004/0059143 | A1 | 3/2004 | Peter et al. | |

FOREIGN PATENT DOCUMENTS

| | | | |
|---|---|---|---|
| CN | 1057407 | A | 1/1992 |
| CN | 1718679 | A | 1/2006 |
| JP | 56-65097 | | 6/1981 |
| JP | 5-504570 | | 7/1993 |

(Continued)

OTHER PUBLICATIONS

Lotero, E. et al., Synthesis of boidiesel via acid catalysis, 2005, Ind. Eng. Chem. Res., vol. 44, pp. 5353-5363.*

(Continued)

*Primary Examiner* — Yate K Cutliff

(74) *Attorney, Agent, or Firm* — Oblon, Spivak, McClelland, Maier & Neustadt, L.L.P.

(57) ABSTRACT

The present invention relates to a process for producing fatty acid alkyl esters from fats/oils and a C1 to C5 lower alcohol as reaction starting materials with a solid catalyst, wherein the starting materials and reaction products in a reaction system where the degree of conversion of fats/oils is 50 mol % or more are reacted in such a state as to be in one-liquid phase, or the starting materials and reaction products in a reaction system at a stage with the highest degree of conversion of fats/oils are reacted in such a state as to be in one-liquid phase.

20 Claims, 3 Drawing Sheets

FOREIGN PATENT DOCUMENTS

| | | | |
|---|---|---|---|
| JP | 2003-507495 | | 2/2003 |
| JP | 2004-533537 | | 11/2004 |
| JP | 2007-254305 | | 10/2007 |
| WO | WO 91/13050 | | 9/1991 |
| WO | WO 01/12581 | A1 | 2/2001 |
| WO | WO 03/004591 | A1 | 1/2003 |
| WO | WO 2005/021697 | A1 | 3/2005 |

OTHER PUBLICATIONS

Zhou, H., et al., Solubility of multicomponent systems in the biodiesel production by transesterificatin of *Jatropha curca* L. oil with methanol, 2006, J. Chem. Eng. Data, vol. 51, No. 3, pp. 1130-1135.*

CN 1718679, Shanxi Coal Chem Inst., 2006, English translation from Dialog, 6 pages.*

Weiyang Zou, et al., "Ethyl Esters from the Single-Phase Base-Catalyzed Ethanolysis of Vegetable Oils", J. Am. Oil Chem. Soc., vol. 80, No. 4, 2003, pp. 367-371.

David G. B. Boocock, et al., "Fast One-Phase Oil-Rich Processes for the Preparation of Vegetable Oil Methyl Esters", Biomass and Bioenergy, vol. 11, No. 1, 1996, pp. 43-50.

Chinese Office Action issued Aug. 31, 2011, in Patent Application No. 200880018456.3.

* cited by examiner

Fig. 3 (Enlargement of part of Fig. 2)
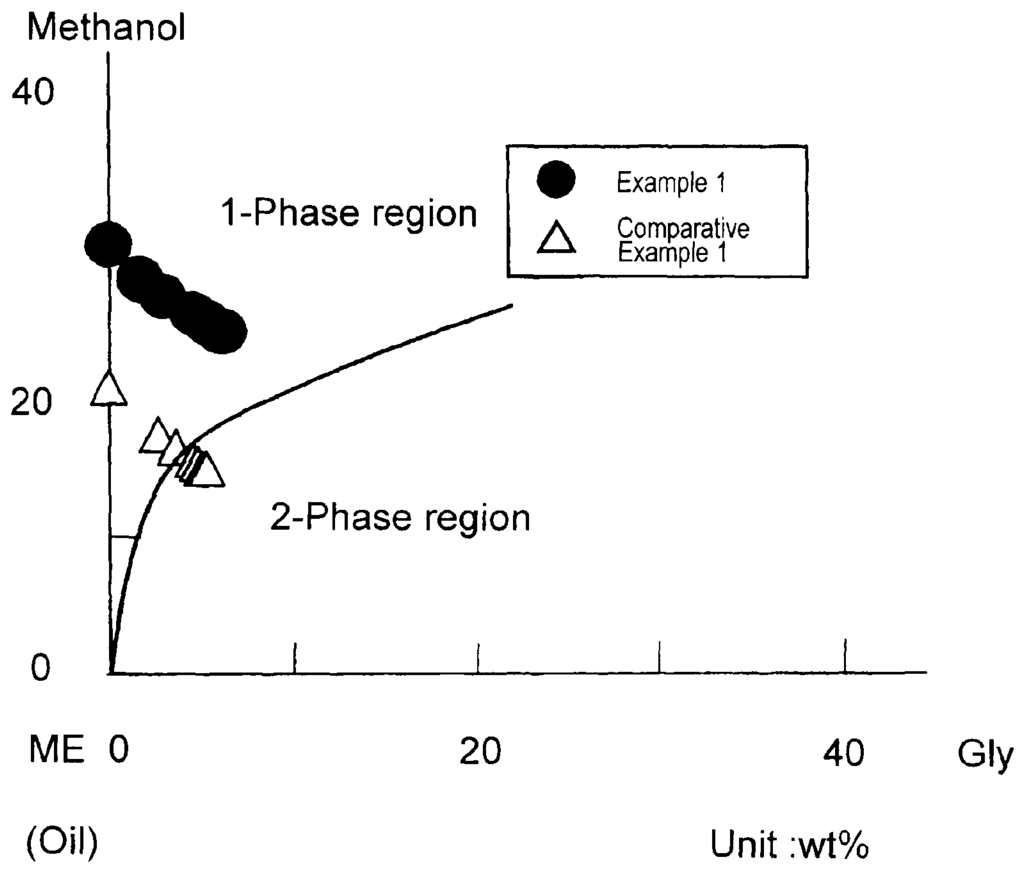

PROCESS FOR PRODUCING FATTY ACID ESTERS

FIELD OF THE INVENTION

The present invention relates to a process for producing fatty acid alkyl esters from fats/oils and lower alcohols with a solid catalyst.

BACKGROUND OF THE INVENTION

As methods of producing fatty acid alkyl esters by ester exchange between triglyceride-based fats/oils and lower alcohols, various methods are known. This reaction for example in JP-A56-65097 is allowed to proceed with an alkali catalyst while glycerin formed by multistage reaction is separated. However, a homogeneous catalyst is used therein thus necessitating a step of neutralization/removal of the catalyst after the ester-exchange reaction, to make a glycerin purification process complicated.

To solve this problem, WO-A05/021697 has reported a process for producing fatty acid alkyl esters by using a solid acid catalyst.

SUMMARY OF THE INVENTION

The present invention provides a process for producing fatty acid alkyl esters from fats/oils and a C1 to C5 lower alcohol as reaction starting materials with a solid catalyst, wherein the starting materials and reaction products in a reaction system where the degree of conversion of fats/oils is 50 mol % or more are reacted in such a state as to be in one-liquid phase.

The present invention provides a process for producing fatty acid alkyl esters from fats/oils and a C1 to C5 lower alcohol as reaction starting materials with a solid catalyst at multi-stages, wherein the starting materials and reaction products in a reaction system in a stage with the highest degree of conversion of fats/oils are reacted in such a state as to be in one-liquid phase.

The present invention provides a process for producing fatty alcohols, including step 1 and step 2:

step 1: producing a oil phase containing fatty acid alkyl esters from fats/oils and a C1 to C5 lower alcohol as reaction starting materials with a solid catalyst, wherein the starting materials and reaction products in a reaction system where the degree of conversion of fats/oils is 50 mol % or more are reacted in such a state as to be in one-liquid phase or wherein the starting materials and reaction products in a reaction system in a stage with the highest degree of conversion of fats/oils are reacted in such a state as to be in one-liquid phase; then separating the lower alcohol from reaction products and subjecting the resulting liquid component to oil/water separation; and step 2: producing fatty alcohols by reacting the oil phase containing fatty acid alkyl esters obtained at the step 1 with hydrogen.

DETAILED DESCRIPTION OF THE INVENTION

WO-A2005/021697 shows, in the Examples, a reaction under the conditions where lower alcohols are gasified, or under the conditions where glycerin undergoes phase separation, and there still remains a task for preventing a reduction in the reaction rate and for prevention of formation of byproducts as a new problem arising from use of a solid acid catalyst.

The present invention provides a process for producing fatty acid alkyl esters highly efficiently in higher yield by maintaining a catalyst activity and preventing a drop in the reaction rate even at the final stage of the reaction and by suppressing an increase in byproducts such as methoxypropanediol produced as a byproduct by reaction of glycerin with a lower alcohol.

In the present invention, the state of the starting materials and reaction products in one-liquid phase in a reaction system refers to a state in which the starting materials that are fats/oils and a C1 to C5 lower alcohol, and the reaction products that are fatty acid alkyl esters and glycerin, occur in one-liquid phase without phase separation of glycerin.

According to the process of the present invention, phase separation of glycerin does not occur so that glycerin can be prevented from acting as a catalyst poison by adsorption onto the active site of a catalyst, resulting in maintenance of the catalyst activity even at the final stage of the reaction and in preventing a drop in the reaction rate, thereby enabling the reaction with a lower amount of the catalyst used. Because phase separation of glycerin does not occur, the concentration of glycerin on the surface of a catalyst is not increased, thus preventing the reaction between glycerin and a lower alcohol from occurring and thereby suppressing an increase in byproducts. Because lower alcohols are not gasified, the concentration of lower alcohols in the liquid can be increased to prevent a drop in the reaction rate.

[Production of Fatty Acid Alkyl Esters (Step 1)]

The fats and oils used in the present invention include naturally occurring vegetable fats and oils and animal fats and oils. The vegetable fats and oils include coconut oil, palm oil, palm kernel oil etc., and the animal fats and oils include tallow, lard, fish oil etc.

The fats and oils may contain, in addition, fatty acids, carbohydrates, sugars, proteins etc. The acid value (mg-potassium hydroxide/g-oils and fats) of the used fats and oils is not limited. In order to suppress degradation of a catalyst, fats and oils having an acid value being preferably 15 or less, more preferably 9 or less, even more preferably 6 or less may be used.

Specific examples of the lower alcohols having 1 to 5 carbon atoms used in the present invention include methanol, ethanol, propanol etc., among which methanol is preferable from the viewpoint of low cost and easy recovery.

The solid catalyst used in the present invention is a powdery catalyst or a molded product thereof or ion-exchange resin, among which a powdery catalyst or a molded product thereof that can be used at a high reaction temperature is preferable. Such catalyst is preferably a solid acid catalyst, more preferably a weakly acidic solid acid catalyst having a strong acid point of 0.2 mmol/g-cat or less and a weak acid point of 0.3 mmol/g-cat or more, each acid point being defined as follows:

Weak acid point: the point at which desorption of $NH_3$ occurs in the range of 100 to 250° C. in TPD (Temperature Programmed Desorption: ammonia adsorption-desorption process)

Strong acid point: the point at which desorption of $NH_3$ occurs in the range of higher than 250° C. in TPD It is further preferable that the weakly acidic solid catalyst is a molded product of a solid acid catalyst having the structure (A), the structure (B) and the metal atom (C) as follows:

Structure (A): a structure of an inorganic phosphoric acid wherein the hydrogen atom is removed from at least one OH group thereof, Structure (B): a structure of an organic phosphoric acid represented by the general formula (1) or (2) below, wherein the hydrogen atom is removed from at least one OH group thereof:

(1)

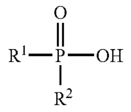

(2)

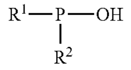

wherein —$R^1$ and —$R^2$ each represent a group selected from —R, —OR, —OH and —H, and at least one of —$R^1$ and —$R^2$ is —R or —OR provided that R is an organic group having 1 to 22 carbon atoms.

Metal atom (C): at least one metal atom selected from the group consisting of aluminum, gallium and iron.

In the structure (A) above, the inorganic phosphoric acid includes orthophosphoric acid or condensed phosphoric acids such as metaphosphoric acid or pyrophosphoric acid. Orthophosphoric acid is preferable in respect of property or performance. In the structure (B), the organic phosphoric acid represented by the general formula (1) or (2) includes phosphonic acid, monophosphonate, phosphinic acid, monophosphate, diphosphate, monophosphite and diphosphite or a mixture thereof, preferably phosphonic acid.

The organic group R in the organic phosphoric acid is preferably an alkyl group such as methyl, ethyl, n-propyl, iso-propyl, n-butyl, iso-butyl, tert-butyl, n-hexyl, 2-ethylhexyl, octyl, dodecyl and octadecyl, and an aryl group such as phenyl and 3-methylphenyl, to which an amino group, alkoxy group, carbonyl group, alkoxycarbonyl group, carboxylic acid group, halogen atom such as chloro group, phosphonic acid group, and sulfonic acid group may be added.

From the viewpoint of performance and/or cost, the metal atom (C) is preferably aluminum. For the purpose of improving selectivity and other performance, the metal atom (C) may contain a small amount of metal atoms other than aluminum, gallium and iron. It is not always necessary that all metal atoms (C) contained in the catalyst are bonded to the structure (A) or (B), and therefore, a part of the metal atoms (C) may be present in the form of metal oxide, metal hydroxide etc.

Another preferable example of the weakly acidic solid acid catalyst used in the present invention is a molded, heterogeneous catalyst containing aluminum orthophosphate, preferably having a pore diameter of 6 to 100 nm, a pore capacity of at least 0.46 ml/g, and an acid content of at least 0.40 mmol/g.

The process for producing the weakly acidic solid acid catalyst used in the present invention includes a precipitation method, a method of impregnating a metal oxide or hydroxide with organic and inorganic phosphoric acids, and a method of replacing an inorganic phosphoric acid group of an inorganic aluminum phosphate gel by an organic phosphoric acid group, among which the precipitation method is preferable.

In preparing the solid catalyst used in the present invention, a carrier having a large surface area may coexist to give the catalyst carried thereon. As the carrier, use can be made of silica, alumina, silica alumina, titania, zirconia, diatomaceous earth, activated carbon etc. When the carrier is used in excess, the content of the active component is decreased and in consequence the activity is lowered, and thus the proportion of the carrier in the catalyst is preferably 90 wt % or less.

In the mode of reaction in the invention, it is possible to use either a bath-type reactor having a stirrer or a fixed-bed reactor packed with a catalyst, and the fixed-bed reactor is preferable from the viewpoint of eliminating the necessity for separation of the catalyst.

The reaction system in the present invention is a reaction system having liquid (lower alcohols)-liquid (fats and oils)-solid (catalyst) where the lower alcohols such as methanol are contacted in a liquid state. In a single-stage reaction, the starting materials and reaction products in a reaction system where the degree of conversion of fats and oils is 50 mol % or more are reacted in such a state as to be in one-liquid phase. In a multistage reaction, the stating materials and reaction products in a reaction system in a stage with the highest degree of conversion of fats and oils are reacted in such a state as to be in one-liquid phase.

In the present invention, the degree of conversion of fats and oils are values obtained according to the following equation:

Degree of conversion of fats and oils (mol %)=(equivalent of starting glyceride−equivalent of unreacted glyceride)/(equivalent of starting glyceride)×100

The equivalent of glyceride refers to the number of moles of fatty acid group possessed by glyceride.

To carry out the reaction in which the reaction materials and reaction products in the reaction system are in such a state as to be in one-liquid phase, the conditions under which phase separation of glycerin does not occur even if the reaction has proceeded to a higher extent, specifically the molar ratio of lower alcohols to fats and oils, the reaction temperature and the reaction pressure are established. That is, it is necessary to increase the molar ratio of lower alcohols to fats and oils and to raise the reaction temperature, in order to prevent phase separation of glycerin. However, when the molar ratio of lower alcohols to fats and oils is high or the reaction temperature is high, the lower alcohols are easily gasified, and thus the reaction is carried out preferably at a pressure higher than the vapor pressure of the lower alcohols at the reaction temperature.

In the present invention, the molar ratio of lower alcohols to fats and oils (calculated as triglycerides) is preferably 7 or more, more preferably 8 or more from attaining an excellent reaction rate. From the viewpoint of effecting the reaction economically by reducing the amount of lower alcohols recovered, the molar ratio of lower alcohols to fats and oils is preferably 150 or less, more preferably 90 or less and even more preferably 45 or less. If necessary, the fats and oils may be diluted with a diluent. The diluent includes, but is not limited to, xylene, toluene, hexane, tetrahydrofuran, acetone, ether, and fatty acid alkyl esters.

The degree of conversion at which the materials come to be in one-liquid phase is preferably 50 mol % or more, more preferably 60 mol % or more, even more preferably 70 mol % or more and even more preferably 80 mol % or more. As the degree of conversion is increased, the concentration of glycerin is increased so that phase separation of glycerin easily occurs, but the materials may be reacted at a high conversion rate in the uniform liquid phase system, thereby making the effect of the present invention more promising.

The reaction temperature is preferably 100° C. or more, more preferably 130° C. or more, even more preferably 150° C. or more and even more preferably 160° C., thereby attaining a sufficient catalyst activity to increase the reaction rate, attaining a desired degree of reaction and preventing phase separation of glycerin. The reaction temperature is preferably 220° C. or less, more preferably 200° C. or less, from the viewpoint of inhibiting the formation of ethers between glycerin such as byproduct methoxypropanediol and a lower alcohol thereby preventing the glycerin purifying step from being complicated.

Based on the vapor pressure of lower alcohols at the reaction temperature, the reaction pressure should be established such that the reaction starting materials and reaction products come to be in one-liquid phase. The reaction pressure is preferably not lower than the vapor pressure of lower alcohols at the reaction temperature. It is preferably 0.1 to 10 MPa-G (G means gauge pressure), more preferably 0.5 to 8 MPa-G and even more preferably 1.5 to 8 MPa-G.

The reaction time varies depending on the reaction conditions (for example, reaction mode, catalyst amount, temperature), but in the reaction in a vessel type reactor, the reaction time may be usually 2 to 10 hours. In the continuous reaction in a fixed-bed reactor, the liquid hourly space velocity (LHSV) of the fats and oils is preferably 0.02/hr or more, more preferably 0.1/hr or more, from the viewpoint of increasing productivity per unit volume of the reactor to effect the reaction economically. From the viewpoint of attaining a sufficient reaction rate, the LHSV is preferably 2.0/hr or less, more preferably 1.0/hr or less.

The reaction products thus obtained contain the objective fatty acid alkyl esters, glycerin etc. A mixture of the reaction materials and reaction products is obtained in the reactor, and this mixture is subjected to evaporation or distillation in a usual manner thereby separating lower alcohols and then is separated into an oil phase and an aqueous phase by allowing to stand, being centrifuged or etc to obtain an aqueous phase containing glycerin and an oil phase containing fatty acid alkyl esters. The acid value of the thus obtained fatty acid alkyl esters is not limited. When the fatty acid alkyl esters is hydrogenated to produce fatty alcohols etc, in order to suppress degradation of a catalyst at the subsequent step, it is preferable to reduce the acid value of the fatty acid alkyl esters down to 1 or less, more preferably 0.7 or less, even more preferably 0.5 or less. The invention proves for producing the fatty acid alkyl esters is a preferable process for producing fatty acid alkyl esters having so low an acid value.

In the present invention, reactors preferably fixed-bed reactors each charged with a solid catalyst are arranged at multistages, and the present invention preferably has a step wherein lower alcohols are separated from reaction products containing fats and oils obtained from the reactor at an upper stage and the resulting liquid component is subjected to oil/water separation to remove glycerin, between the reactor at an upper stage and the reactor at a lower stage. The upstream side refers to a side nearer to the fixed-bed reactor to which starting fats and oils are first fed. When the multistage reaction is carried out, the reaction at each stage has "start" and "end". In the case of the multistage reaction, the reaction at least at a stage with the highest degree of conversion among the respective stages is carried out under the conditions where the reaction materials and reaction products come to be in one-liquid phase. This means that the reaction at the stage with the highest glycerin content is carried out in a uniform liquid phase, thereby bringing about the highest effect of the present invention. As a matter of course, the reaction at all stages may be carried out in a uniform liquid phase.

[Process for Producing Fatty Alcohols (Step 2)]

The process for producing fatty alcohols according to the present invention is a process wherein the fatty acid alkyl esters obtained by the above-described process of the invention are subjected to hydrogenation reaction to give fatty alcohols. As used herein, the fatty alcohols refer to alcohols derived from fats and oils.

The hydrogenation catalyst in this process can be used a generally known copper-based catalyst or a noble metal-based catalyst such as catalysts based on palladium or platinum. The copper catalyst can include catalysts such as those made of copper-chrome, copper-zinc, copper-iron-aluminum, copper-silica, etc.

The hydrogenation reaction can be carried out in the presence of a hydrogenation catalyst in any generally used reaction systems such as a liquid phase suspension bed system or a fixed bed system.

When the hydrogenation reaction is carried out in a liquid phase suspension bed system, the amount of the hydrogenation catalyst can be selected arbitrarily in such a range as to achieve practical reaction yield, depending on reaction temperature and reaction pressure, but preferably the amount of the catalyst is 0.1 to 20 wt % based on the fatty acid alkyl esters. The reaction temperature is preferably 160 to 350° C., more preferably 200 to 280° C. The reaction pressure is preferably 0.1 to 35 MPa, more preferably 3 to 30 MPa.

When the hydrogenation reaction is continuously carried out in a fixed bed system, the hydrogenation catalyst is molded preferably in a cylindrical, pellet or spherical form. The reaction temperature is preferably 130 to 300° C., more preferably 150 to 270° C., and the reaction pressure is preferably 0.1 to 30 MPa. In consideration of productivity and reactivity, the LHSV can be determined arbitrarily depending on the reaction conditions.

Since the fatty acid alkyl esters can be produced effectively by the production process of step I, fatty alcohols can be also produced effectively by hydrogenating the fatty acid alkyl esters. It is preferable to production of the fatty alcohols because the fatty acid alkyl esters produced at step I has a low acid value.

BRIEF DESCRIPTION OF THE DRAWINGS

FIG. 3 is an enlargement of a part of FIG. 2, to clearly show data in FIG. 2 for Comparative Example 1.

EXAMPLES

Figure 1:
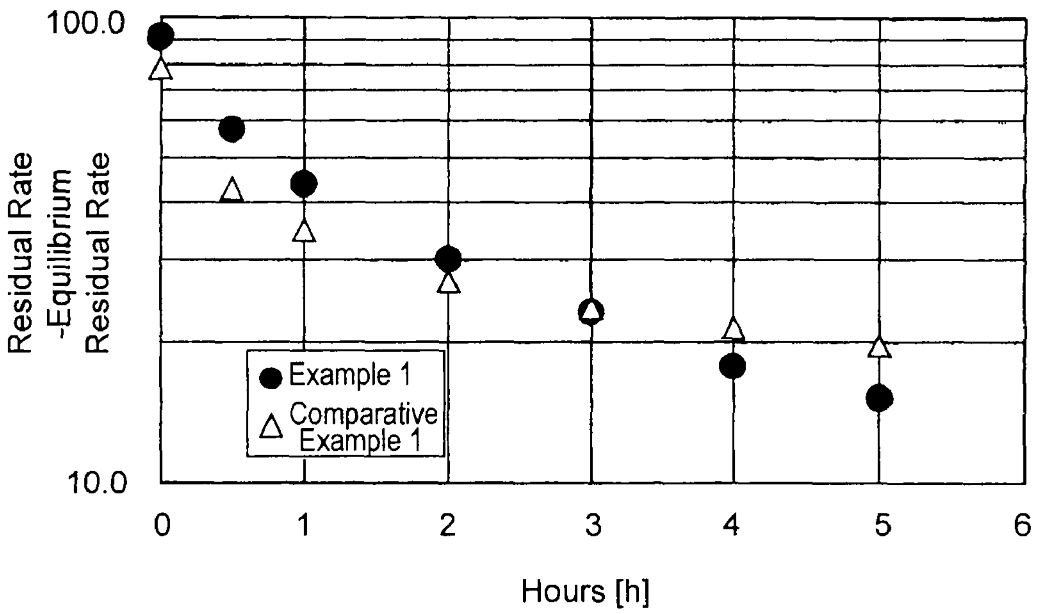
FIG. 1 is a graph showing the relationship between the reaction time and the residual ratio-equilibrium residual ratio in Example 1 and Comparative Example 1.

Hereinafter, the present invention is described in more detail by reference to the Examples. However, the Examples are set forth for mere illustration of the present invention and are not intended to limit the present invention.

Catalyst Production Example 1

9.9 g of ethyl phosphonic acid, 27.7 g of 85% orthophosphoric acid, and 112.5 g of aluminum nitrate.$9H_2O$ were dissolved in 1000 g water. Aqueous ammonia was added dropwise to this mixed solution at room temperature (25° C.) until the pH was increased to 5. During this step, gelled white precipitates were formed. The precipitates were collected by filtration, washed with water, dried at 110° C. for 15 hours and pulverized to a size of 60-mesh or less. Alumina sol was added in a final content of 10% to the resulting pulverized catalyst, and the catalyst was extrusion-molded into 1.5-mmϕ pieces. These pieces were calcinated at 250° C. for 3 hours to give a molded catalyst consisting of a solid acid catalyst (referred to hereinafter as catalyst 1). The weak acid point of the resulting catalyst was 1 mmol/g, and the strong acid point was below the limit of detection.

Example 1

A 500-ml autoclave was charged with 200.0 g of refined palm kernel oil having an acid value of 0.2 mg-potassium hydroxide/g-fats and oils (hereinafter using the same unit as here) and with 92.9 g of methanol (10-fold molar excess relative to fats and oils (calculated as triglycerides) in the palm kernel oil). After 10.0 g of the catalyst 1 was introduced into a basket, the mixture was reacted at 170° C. for 5 hours under stirring at 900 rpm. The reaction pressure was 2 MPa-G. Sampling of the reaction mixture was carried out 0, 0.5, 1, 2, 3, 4 and 5 hours after initiation of the reaction, then separated with water into a glycerin layer and an oil layer and subjected to analysis.

<Method of Analyzing the Oil Layer>

The sample solution was treated for about 10 minutes with a TMS-converting agent (trade name: TMSI-H, manufactured by GL Sciences, Inc.) thereby converting the sample into TMS derivative and then analyzed by gas chromatography.

Conditions for Gas Chromatography

Gas chromatographic unit: HP6890 manufactured by Hewlett-Packard development company Temperature rising program: 60° C. (2 min)→10° C./min→350° C. (15 min)

Split mode: (ratio 15:1), split flow rate 60 mL/min., He pressure 144 kPa

Column: Ultra-Alloy-1 (HT) manufactured by Frontier Laboratories Ltd., length 15 m, film thickness 0.15 μm, inner diameter 0.25 mm Injection port temperature: 300° C.

Detector (FID) temperature: 350° C., hydrogen 30 mL/min., air 300 mL/min., makeup 28 mL/min.

<Method of Analyzing the Glycerin Layer>

Conditions for Gas Chromatography

Gas chromatographic unit: HP5890 manufactured by Hewlett-Packard

Temperature rising program: 40° C. (2 min)→410° C./min→4180° C. (20 min)

Split mode: He pressure 144 kPa

Column: DB-WAX manufactured by J&W, length 30 m, film thickness 0.25 inner diameter 0.25 mm Injection port temperature: 250° C.

Detector (FID) temperature: 250° C.

The same analysis was also conducted in the Examples and Comparative Examples that follow.

FIG. 1 shows the relationship between the reaction time and the residual ratio-equilibrium residual ratio in the oil layer. As is evident from FIG. 1, the residual ratio—equilibrium residual ratio in the oil layer was reduced with time to reach 15.3 mol % after 5 hours. The degree of conversion of fats and oils at this time is 79.9 mol %. The acid value of the fatty acid methyl ester was 0.5. The residual ratio is expressed as (equivalent of unreacted glyceride)/(equivalent of starting glyceride)×100. The equilibrium residual ratio is a residual ratio when the reaction is equilibrated. That is, as the number of moles is increased, the degree of conversion is increased and the equilibrium residual ratio is decreased in relationship to the reaction equilibrium, and by comparing the rate of reduction in the residual ratio-equilibrium residual ratio, the rate of reaction independent of the equilibrium can be discussed. The equilibrium residual ratio in Example 1 is 4.8 mol %.

Figure 2:
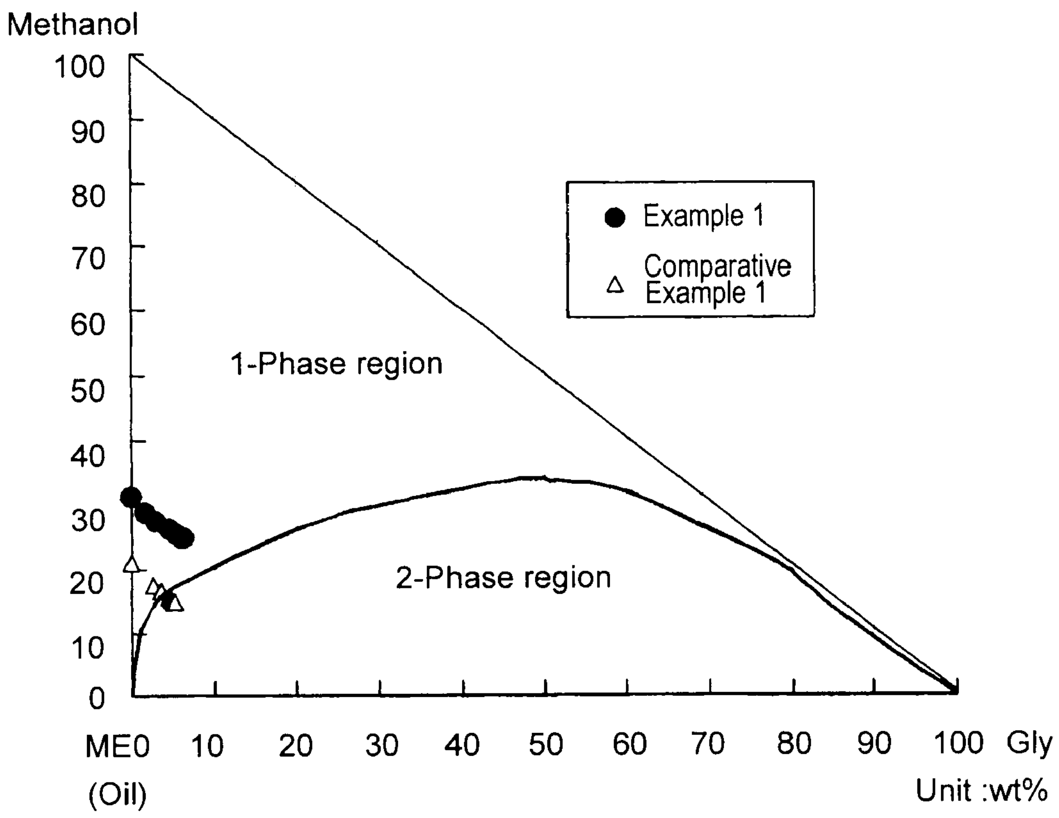
FIG. 2 is a phase diagram of methyl ester-glycerin-methanol during the reaction in Example 1 and Comparative Example 1.

FIGS. 2 and 3 (an enlarged drawing of FIG. 2) show a phase diagram of methyl ester-glycerin-methanol during the reaction. In this example, glycerin was in one-liquid phase without phase separation throughout the reaction. Whether phase separation of glycerin occurred or not was visually evaluated.

Comparative Example 1

A 500-ml autoclave was charged with 200.0 g of refined palm kernel oil having an acid value of 0.2 and with 55.8 g of methanol (6-fold molar excess relative to fats and oils (calculated as triglycerides) in the palm kernel oil). After 10.0 g of the catalyst 1 was introduced into a basket, the mixture was reacted at 170° C. for 5 hours under stirring at 900 rpm. The reaction pressure was 2 MPa-G. The reaction mixture was sampled in the same manner as in Example 1, then separated with water into a glycerin layer and an oil layer and subjected to analysis.

FIG. 1 shows the relationship between the reaction time and the residual ratio-equilibrium residual ratio in the oil layer. As is evident from FIG. 1, the residual ratio-equilibrium residual ratio in the oil layer was reduced with time, but 2 hours later and thereafter, was reduced at a lower rate to reach 19.8 mol % after 5 hours. The equilibrium residual ratio in Comparative Example 1 is 12.8 mol %. The degree of conversion of fats and oils at this time is 67.3 mol %. The acid value of fatty acid methyl ester is 0.4.

FIGS. 2 and 3 (an enlarged drawing of FIG. 2) show a phase diagram of methyl ester-glycerin-methanol during the reaction. In this example, phase separation of glycerin was initiated after about 2 hours of the reaction. It can be seen that when such phase separation of glycerin occurs, phase-separating glycerin is adsorbed onto the surface of the catalyst to cause a reduction in the catalyst activity, resulting in a reduction in the reaction rate.

Example 2

Two tube reactors each having an inner diameter of 35.5 mmϕ and a length of 800 mmH, having a tube of 6 mm in inner diameter for temperature measurement in the axial direction, were connected in series and each tube was packed with 500 cc of the catalyst 1. Refined coconut oil having an acid value of 0.3 was used as the fats and oils and fed together with liquid methanol into the top of the reactor and reacted at a reaction temperature of 170° C. at an LHSV of 0.2, at a reaction pressure of 3.0 MPa-G. The molar amount of methanol fed was 20 times as much as the molar amount (calculated as triglycerides) of the fats and oils. In this example, the phase separation of glycerin did not occur throughout the reaction. After the reaction was finished, the reaction solution was separated, by adding water, into a glycerin layer and an oil layer and analyzed, and as a result, the methyl ester in the oil layer was 95.3% by weight, acid value was 0.2, methoxypropanediol (MPD) as a byproduct in the glycerin layer was 2.3% by weight, and the degree of conversion of the fats and oils was 96.2 mol %.

Comparative Example 2

The reaction was carried out in the same manner as in Example 2 except that the amount of methanol fed was 6 times as much as the molar amount (calculated as triglycerides) of fats and oils. In this example similar to Comparative Example 1, phase separation of glycerin occurred as the reaction proceeded. After the reaction was finished, the reaction solution was separated with water into a glycerin layer and an oil layer and subjected to analysis. The results indicated that the methyl ester in the oil layer was 71.9% by weight, acid value was 0.3, methoxypropanediol (MPD) as a byproduct in the glycerin layer was 2.9% by weight, and the degree of conversion of the fats and oils was 74.1 mol %. In this example, the amount of MPD formed was higher in spite of a lower degree of conversion of the fats and oils than in Example 2.

Example 3

The reaction was carried out in the same manner as in Example 2 except that the amount of methanol fed was 10 times as much as the molar amount (calculated as triglycerides) of fats and oils. In this example, phase separation of glycerin did not occur throughout the reaction. After the reaction was finished, the reaction solution was separated with water into a glycerin layer and an oil layer and subjected to analysis. The results indicated that the methyl ester in the oil layer was 88.8% by weight, acid value was 0.3, methoxypropanediol (MPD) as a byproduct in the glycerin layer was 2.8% by weight, and the degree of conversion of the fats and oils was 90.5 mol %.

Comparative Example 3

The reaction was carried out in the same manner as in Example 3 except that the reaction pressure was 1.0 MPa-G. In this example, a part of methanol was gasified. After the reaction was finished, the reaction solution was separated with water into a glycerin layer and an oil layer and subjected to analysis. The results indicated that the methyl ester in the oil layer was 58.7% by weight, an acid value was 0.1, methoxypropanediol (MPD) as a byproduct in the glycerin layer was 3.7% by weight, and the degree of conversion of the fats and oils was 60.7 mol %.

The reaction conditions and results in Examples 2 to 3 and Comparative Examples 2 to 3 are collectively shown in Table 1.

TABLE 1

| | | Example | | Comparative example | |
|---|---|---|---|---|---|
| | | 2 | 3 | 2 | 3 |
| Reaction method | (—) | Continuous | Continuous | Continuous | Continuous |
| Molar ratio of lower alcohols to fats and oils | (—) | 20 | 10 | 6 | 10 |
| Raction temperature | (° C.) | 170 | 170 | 170 | 170 |
| Reaction pressure | (MPa-G) | 3.0 | 3.0 | 3.0 | 1.0 |
| Liquid hourly space velocity (LHSV) | ($hr^{-1}$) | 0.2 | 0.2 | 0.2 | 0.2 |
| Content of methyl ester in the oil layer | (wt %) | 95.3 | 88.8 | 71.9 | 58.7 |
| Content of MPD in the glycerin layer*[1] | (wt %) | 2.3 | 2.8 | 2.9 | 3.7 |

*[1]MPD: methoxypropanediol

Example 4

A tube reactor of 237.2 mmφ in inner diameter was packed with 45000 cc of the catalyst 1. Refined coconut oil having an acid value of 5.8 was used as the fats and oils and fed together with liquid methanol into the top of the reactor and reacted at a reaction temperature of 170° C. at an LHSV of 0.4, at a reaction pressure of 3.0 MPa-G. The molar amount of methanol fed was 10 times as much as the molar amount (calculated as triglycerides) of the fats and oils. The phase separation of glycerin did not occur throughout the reaction. The reaction solution was fed to an evaporator, and the methanol was evaporated at a pressure of 0.1 MPa-G at 150° C. The content of methanol in the oil phase was 1.1 wt %. Thereafter, the liquid sample was left and thereby separated at 50° C. into an oil phase and an aqueous phase. The methyl ester in the resulting oil phase was 79 wt %, the acid value was 0.5 and the glycerin concentration was 0.3 wt %. 180 g of the oil layer was reacted again with liquid methanol in 10-fold molar excess relative to the fats and oils (calculated as triglycerides) in the presence of 9 g of the catalyst 1 in an autoclave. The temperature was 170° C., the pressure was 1.6 MPa-G, and the reaction time was 6 hours. The phase separation of glycerin did not occur throughout the reaction. The resulting reaction product was separated into oil and aqueous phases and analyzed, and as a result, the methyl ester in the oil phase was 97% by weight, and the degree of formation of methoxypropanediol (MPD) as a byproduct was 2% by weight relative to glycerin.

Example 5

The oil phase obtained in Example 4 was further reacted in the same reactor thereby giving an oil phase containing 99.4 wt % fatty acid methyl ester. Water was added in a final content of 2 wt % to the resulting oil phase, then stirred for 30 minutes and left for 1 hour to separate it into oil and aqueous phases, followed by rectification to give fatty acid methyl esters. Then, the resulting fatty acid methyl esters were subjected to hydrogenation reaction in a fixed bed reactor having a column packed with 259 mL titania-supported copper—zinc catalyst (composition: Cu=35%, Zn=1.8%, 50% $TiO_2$ carrier, in the form of 3.2 mmφ×3.2 mm cylinder) to give fatty alcohols. The hydrogenation reaction was conducted under the conditions of a pressure of 19.6 MPa-G and a temperature of 220° C. The feed rate of fatty acid methyl esters was 187 mL/h, and the flow rate of hydrogen was 414 NL/h.

The invention claimed is:

1. A process for producing fatty acid alkyl esters comprising: reacting, in a reactor, fats/oils and a C1 to C5 lower alcohol as reaction starting materials in the presence of a solid catalyst, wherein the starting materials and reaction products in a reaction system where the degree of conversion of fats/oils is 50 mol % or more are reacted in one-liquid phase without phase separation of glycerin.

2. A process for producing fatty acid alkyl esters comprising: reacting, in a reactor, fats/oils and a C1 to C5 lower alcohol as reaction starting materials in the presence of a solid catalyst at multi-stages, wherein the starting materials and reaction products in a reaction system in a stage with the highest degree of conversion of fats/oils are reacted in one-liquid phase without phase separation of glycerin.

3. The process for producing fatty acid alkyl esters according to claim 1, wherein the molar ratio of the lower alcohol to the fats/oils is from 7 to 150.

4. The process for producing fatty acid alkyl esters according to claim 1, wherein a reaction temperature is 100 to 220° C.

5. The process for producing fatty acid alkyl esters according to claim 1, wherein a reaction pressure is higher than a vapor pressure of the lower alcohol at a reaction temperature.

6. The process for producing fatty acid alkyl esters according to claim 2, which further comprises separating the lower alcohol from reaction products having fats and oils obtained from the reactor at an upper stage and subjecting the resulting liquid component to oil/water separation to remove glycerin, between the reactor at an upper stage and the reactor at a lower stage.

7. A process for producing fatty alcohols, comprising:

a) producing a oil phase comprising fatty acid alkyl esters from fats/oils and a C1 to C5 lower alcohol as reaction starting materials with a solid catalyst, wherein the starting materials and reaction products in a reaction system where the degree of conversion of fats/oils is 50 mol % or more are reacted in one-liquid phase without phase separation of glycerin or wherein the starting materials and reaction products in a reaction system in a stage with the highest degree of conversion of fats/oils are reacted in one-liquid phase without phase separation of glycerin; then separating the lower alcohol from reaction products and subjecting the resulting liquid component to oil/water separation; and b) producing fatty alcohols by reacting the oil phase comprising fatty acid alkyl esters obtained from said a) producing with hydrogen.

8. The process for producing fatty acid alkyl esters according to claim 2, wherein the molar ratio of the lower alcohol to the fats/oils is from 7 to 150.

9. The process for producing fatty acid alkyl esters according to claim 2, wherein a reaction temperature is 100 to 220° C.

10. The process for producing fatty acid alkyl esters according to claim 3, wherein a reaction temperature is 100 to 220° C.

11. The process for producing fatty acid alkyl esters according to claim 2, wherein a reaction pressure is higher than a vapor pressure of the lower alcohol at a reaction temperature.

12. The process for producing fatty acid alkyl esters according to claim 3, wherein a reaction pressure is higher than a vapor pressure of the lower alcohol at a reaction temperature.

13. The process for producing fatty acid alkyl esters according to claim 4, wherein a reaction pressure is higher than a vapor pressure of the lower alcohol at the reaction temperature.

14. The process for producing fatty acid alkyl esters according to claim 3, which further comprises separating the lower alcohol from reaction products having fats and oils obtained from the reactor at an upper stage and subjecting the resulting liquid component to oil/water separation to remove glycerin, between the reactor at an upper stage and the reactor at a lower stage.

15. The process for producing fatty acid alkyl esters according to claim 1, wherein the solid catalyst is a solid acid catalyst.

16. The process for producing fatty acid alkyl esters according to claim 2, wherein the solid catalyst is a solid acid catalyst.

17. The process for producing fatty acid alkyl esters according to claim 7, wherein the solid catalyst is a solid acid catalyst.

18. The process for producing fatty acid alkyl esters according to claim 15, wherein the solid acid catalyst is a weakly acidic solid acid catalyst having a strong acid point of 0.2 mmol/g-cat or less and a weak acid point of 0.3 mmol/g-cat or more.

19. The process for producing fatty acid alkyl esters according to claim 16, wherein the solid acid catalyst is a weakly acidic solid acid catalyst having a strong acid point of 0.2 mmol/g-cat or less and a weak acid point of 0.3 mmol/g-cat or more.

20. The process for producing fatty acid alkyl esters according to claim 17, wherein the solid acid catalyst is a weakly acidic solid acid catalyst having a strong acid point of 0.2 mmol/g-cat or less and a weak acid point of 0.3 mmol/g-cat or more.

* * * * *